United States Patent [19]

Neuzil et al.

[11] 4,349,668

[45] Sep. 14, 1982

[54] PROCESS FOR SEPARATING GLUCOSE FROM FRUCTOSE BY SELECTIVE ADSORPTION

[75] Inventors: Richard W. Neuzil, Downers Grove; James W. Priegnitz, Elgin, both of Ill.

[73] Assignee: UOP Inc., Des Plaines, Ill.

[21] Appl. No.: 197,874

[22] Filed: Oct. 17, 1980

Related U.S. Application Data

[63] Continuation-in-part of Ser. No. 690,769, May 27, 1976, abandoned.

[51] Int. Cl.³ .............................................. C07H 1/06
[52] U.S. Cl. ................................... 536/127; 536/124; 127/46.1; 127/46.3
[58] Field of Search ................ 536/1; 127/46 R, 46 B

[56] References Cited

U.S. PATENT DOCUMENTS 4,014,711  3/1977  Odawara et al. ..................... 536/1

*Primary Examiner*—Johnnie R. Brown
*Attorney, Agent, or Firm*—James R. Hoatson, Jr.; Louis A. Morris; William H. Page, II

[57] ABSTRACT

A process for separating a glucose from a feed mixture comprising glucose and fructose which process comprises contacting the mixture with an adsorbent comprising an X zeolite containing potassium cations at the exchangeable cationic sites thereby selectively adsorbing glucose from the feed mixture and thereafter recovering the glucose. Preferably the glucose will be recovered by desorption from the adsorbent with a desorbent material.

8 Claims, 1 Drawing Figure

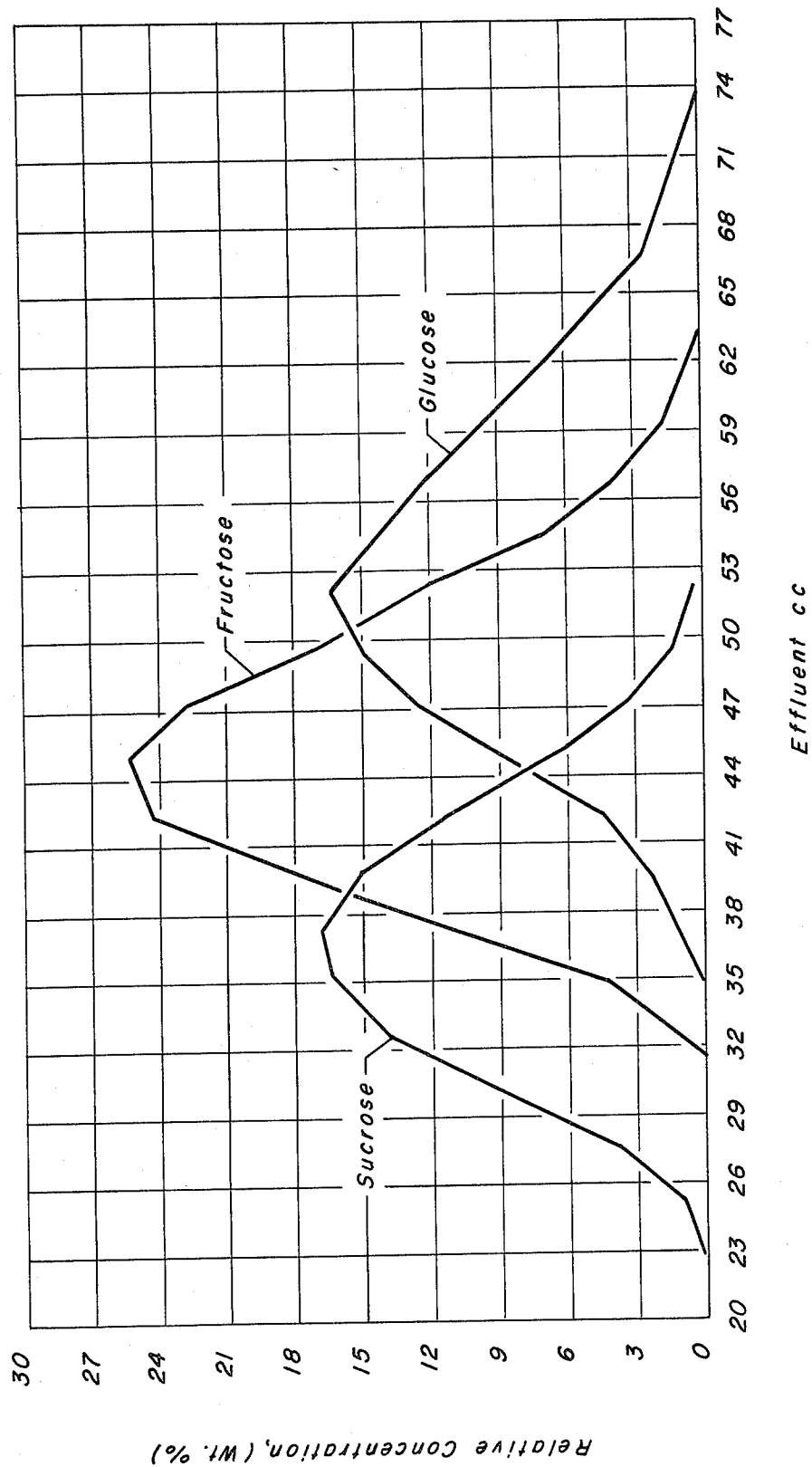

PROCESS FOR SEPARATING GLUCOSE FROM FRUCTOSE BY SELECTIVE ADSORPTION

CROSS REFERENCE TO RELATED APPLICATION

This application is a continuation-in-part of our prior copending application Ser. No. 690,769, filed May 27, 1976, and now abandoned incorporated herein by reference.

BACKGROUND OF THE INVENTION

1. Field of the Invention

The field of art to which this invention pertains is the solid-bed adsorptive separation of monosaccharides. More specifically the invention relates to a process for separating glucose from a mixture comprising glucose and fructose which process employs an adsorbent comprising a crystalline aluminosilicate which selectively adsorbs glucose from the feed mixture.

2. Description of the Prior Art

It is well-known in the separation art that certain crystalline aluminosilicates can be used to separate hydrocarbon types from mixtures thereof. As a few examples, a separation process disclosed in U.S. Pat. Nos. 2,985,589 and 3,201,491 uses a type A zeolite to separate normal paraffins from branched-chain paraffins and processes described in U.S. Pat. Nos. 3,265,750 and 3,510,423 use type X or type Y zeolites to separate olefinic hydrocarbons from paraffinic hydrocarbons. In addition to their use in processes for separating hydrocarbon types, X and Y zeolites have been employed in processes to separate individual hydrocarbon isomers. As a few examples, adsorbents comprising X and Y zeolites are used in the process described in U.S. Pat. No. 3,114,782 to separate alkyl-trisubstituted benzene isomers; in the process described in U.S. Pat. No. 3,864,416 to separate alkyl-tetrasubstituted monocyclic aromatic isomers; in the process described in U.S. Pat. No. 3,668,267 to separate specific alkyl-substituted naphthalenes. Because of the commercial importance of para-xylene, perhaps the more well-known and extensively used hydrocarbon isomer separation processes are those for separating para-xylene from a mixture of C$_8$ aromatics. In processes described in U.S. Pat. Nos. 3,558,730; 3,558,732; 3,626,020; 3,663,638; and 3,734,974 for example adsorbents comprising particular zeolites are used to separate para-xylene from feed mixtures comprising para-xylene and at least one other xylene isomer by selectively adsorbing para-xylene over the other xylene isomers.

In contrast, our invention relates to the separation of non-hydrocarbons and more specifically to the separation of monosaccharides. We have surprisingly discovered that an adsorbent comprising an X zeolite containing potassium cations at the exchangeable cationic sites uniquely exhibits adsorptive selectivity for an aldose with respect to a ketose, particularly glucose with respect to fructose, thereby making separation of glucose from a mixture comprising glucose and fructose by solid-bed selective adsorption possible. Glucose (dextrose) is widely used in confectionery and baking industries, in canning of fruits and vegetables, in beverages and other products requiring sweeteners, and for the preparation of caramel color. In some instances it is used directly as replacement, wholly or in part, for cane or beet sugar; in other instances the special properties of glucose are utilized. While high-purity glucose is readily manufactured from starch (which is made up exclusively of glucose units) by hydrolysis with mineral acids at elevated temperature followed by refining and crystallization of the hydrolyzate, this embodiment of our process is primarily intended for separating glucose from a feed mixture such as an invert sugar solution containing both glucose and fructose to obtain two product streams; an extract product stream containing glucose in a higher concentration than that found in the feed mixture and a raffinate product stream containing fructose in a higher concentration than that found in the feed mixture. Both products can be employed in many commercial uses requiring sweeteners. The raffinate product stream, containing a high concentration of fructose, is of particular commercial interest since fructose is considered to be the most soluble and the sweetest of the sugars. Relative to sucrose having a sweetness of 1.0, fructose has a relative sweetness of about 1.4 while that of glucose is 0.7.

SUMMARY OF THE INVENTION

It is accordingly a broad objective of our invention to provide a process for separating glucose from a feed mixture containing glucose and fructose to produce a glucose product stream and fructose product stream containing higher concentrations of glucose and fructose respectively than were contained in the feed mixture. More specifically it is an objective of our invention to provide a process for separating glucose from a feed mixture, such as an invert sugar solution or a corn syrup, containing glucose and fructose.

In brief summary our invention is, in one embodiment, a process for separating glucose from a mixture thereof with fructose which comprises contacting a mixture containing glucose and fructose, at a temperature in the range of from 20° C. to 200° C. and a pressure in the range of from atmospheric to 500 psig, with an X zeolite containing potassium cations at exchangeable cationic sites and selectively adsorbing glucose in said zeolite to separate the same from unadsorbed fructose, and thereafter removing the adsorbed glucose from the zeolite.

In another embodiment our invention is a process for separating glucose from a mixture comprising glucose and fructose which process comprises the steps of: (a) contacting the mixture at a temperature within the range of from 20° C. to 200° C. and a pressure from atmospheric pressure to 500 psig with an adsorbent comprising an X zeolite containing potassium cations at exchangeable cationic sites, thereby selectively adsorbing glucose; (b) removing from the adsorbent a raffinate stream comprising the fructose; (c) contacting the adsorbent at a temperature within the range of from 20° C. to 200° C. and a pressure from atmospheric pressure to 500 psig with a desorbent material to effect the desorption of the glucose from the adsorbent; and (d) removing from the adsorbent an extract stream comprising the glucose.

Other objectives and embodiments of our invention encompass details about feed mixtures, adsorbents, desorbent materials and operating conditions all of which are hereinafter disclosed in the following discussion of each of the facets of the present invention.

DESCRIPTION OF THE INVENTION

At the outset the definitions of various terms used throughout the specification will be useful in making clear the operation, objects and advantages of our process.

A feed mixture is a mixture containing one or more extract components and one or more raffinate components to be separated by our process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process, an aldose is an extract component and a ketose is a raffinate component. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate steam can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" means products produced by the process containing, respectively, an extract component and a raffinate component in higher concentrations than those found in the extract stream and the raffinate stream. Although it is possible by the process of this invention to produce a high-purity aldose product or a high-purity ketose product (or both) at high recoveries, it will be appreciated that an extract component is never completely adsorbed by the adsorbent, nor is a raffinate component completely non-adsorbed by the adsorbent. Therefore, varying amounts of a raffinate component can appear in the extract stream and, likewise, varying amounts of an extract component can appear in the raffinate stream depending upon the process operating conditions employed. The extract and raffinate streams then are further distinguished from each other and from the feed mixture by the ratio of the concentrations of an extract component and a raffinate component appearing in the particular stream. More specifically, the ratio of the concentration of an aldose (glucose) to that of a less selectively adsorbed ketose (fructose) will be lowest in the raffinate stream, next highest in the feed mixture, and the highest in the extract stream. Likewise, the ratio of the concentration of a less selectively adsorbed ketose (fructose) to that of the more selectively adsorbed aldose (glucose) will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components. The selective pore volume of an adsorbent can in certain instances adsorb portions of raffinate components from the fluid surrounding the adsorbent since in certain instances there is competition between extract components and raffinate components for adsorptive sites within the selective pore volume. If a large quantity of a raffinate component with respect to an extract component surrounds the adsorbent, the raffinate component can be competitive enough to be adsorbed by the adsorbent.

Feed mixtures which can be charged to the process of our invention will be those comprising an aldose and a ketose and more specifically and preferably will be aqueous solutions of glucose and fructose. While the feed mixture may contain more than one aldose and more than one ketose, typically the feed mixture will contain glucose and fructose each in concentrations of from about 0.5 wt. % to about 30 wt. % and more preferably from about 1 to about 15 wt. %. The process may be used to separate an aldopentose from a ketopentose but more typically will be used to separate an aldohexose from a ketohexose. Well-known aldohexoses are glucose (dextrose), mannose and galactose while lesser known aldohexoses are gulose, talose, allose, altrose, and idose; well-known ketohexoses are fructose (levulose) and sorbose. Our process in a preferred embodiment will be used to separate glucose from a feed mixture containing glucose and fructose. Preferred feed mixtures will be aqueous solutions of invert sugar, formed when sucrose is hydrolyzed by acidic materials into equi-molar amounts of glucose and fructose. Other preferred feed mixtures will be aqueous solutions of corn syrup, produced by the enzmatic isomerization of glucose solutions. Typically corn syrup will contain 50–55% glucose and 40–45% fructose.

Desorbent materials used in various prior art adsorptive separation processes vary depending upon such factors as the type of operation employed. In the swing-bed system in which the selectively adsorbed feed component is removed from the adsorbent by a purge stream desorbent selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic adsorbents and which are generally operated at substantially constant pressures and temperatures to insure liquid phase, the desorbent material relied upon must be judiciously selected to satisfy, hopefully, all of several criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material the purity of the extract product and the raffinate product would not be very high, nor would the desorbent material be available for reuse in the process. It is contemplated that at least a portion of the desorbent material will be separated from the extract and the raffinate streams by distillation but other separation methods such as reverse osmosis may also be employed alone or in combination with distillation. Since the raffinate and extract products are foodstuffs intended for human consumption, desorbent materials should also be non-toxic. Finally, desorbent materials should also be materials which are preferably readily available and therefore reasonable in cost. We have found that water satisfies these criteria and is a suitable desorbent material for our process.

The prior art has also recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. Relative selectivity is shown as Equation 1 below.

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally desorbent materials should have a selectivity equal to about 1 or less than 1 with respect to all extract components so that all of the extract components can be extracted as a class and all raffinate components clearly rejected into the raffinate stream. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity the easier the separation is to perform. Higher selectivities permit a smaller amount of adsorbent to be used. The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular aldose or ketose or both all diluted in desorbent is injected for a duration of several minutes. Desorbent flow is resumed, and the tracer and the aldose and ketose are eluted as in a liquid-solid chromatographic operation. The effluent can be analyzed onstream or alternatively effluent samples can be collected periodically and later analyzed separately by analytical equipment and traces of the envelopes of corresponding component peaks developed.

From information derived from the test adsorbent performance can be rated in terms of void volume, retention volume for an extract or a raffinate component, selectivity for one component with respect to the other, and the rate of desorption of an extract component by the desorbent. The retention volume of an extract component may be characterized by the distance between the center of the peak envelope of the extract component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous countercurrent liquid-solid contacting device. The general operating principles of such a device have been previously described and are found in Broughton U.S. Pat. No. 2,985,589. A specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the Americal Chemical Society, Los Angeles, Calif., Mar. 28 through Apr. 2, 1971.

Adsorbents to be used in the process of this invention will comprise a specific crystalline aluminosilicate or molecular sieve. The particular crystalline aluminosilicate encompassed by the present invention will be one in which the alumina and silica tetrahedra are intimately connected in an open three dimensional network to form cage-like structures. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves" particularly when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" although widely used is not strictly suitable since the separation of an aldose from a ketose apparently is dependent on differences in electrochemical attraction of an aldose and the adsorbent and a ketose and the adsorbent rather than on physical size differences in the molecules.

In hydrated form, the crystalline aluminosilicates generally encompass those zeolites represented by the Formula 1 below:

Formula 1

where "M" is a cation which balances the electrovalence of the aluminum-centered tetrahedra and which is generally referred to as an exchangeable cationic site, "n" represents the valence of the cation, "w" represents the moles of $SiO_2$, and "y" represents the moles of water. The generalized cation "M" may be monovalent, divalent or trivalent or mixtures thereof.

The prior art has generally recognized that adsorbents comprising X and Y zeolites can be used in certain adsorptive separation processes. These zeolites are described and defined in U.S. Pat. Nos. 2,882,244 and 3,120,007 respectively which patents are incorporated herein by reference thereto. The X zeolite in the hydrated or partially hydrated form can be represented in terms of mole oxides as shown in Formula 2 below:

Formula 2

$$(0.9\pm0.2)M_{2/n}O:Al_2O_3:(2.5\pm0.5)SiO_2:yH_2O$$

where "M" represents at least one cation having a valence of not more than 3, "n" represents the valence of "M", and "y" is a value up to about 9 depending upon the identity of "M" and the degree of hydration of the crystal. As noted from Formula 2 the $SiO_2/Al_2O_3$ mole ratio of X zeolite is 2.5±0.5. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation "M" is usually predominately sodium and the zeolite is therefore referred to as a sodium-X zeolite. Depending upon the purity of the reactants used to make the zeolite, other cations mentioned above may be present, however, as impurities. The Y zeolite in the hydrated or partially hydrated form can be similarly represented in terms of mole oxides as in Formula 3 below:

Formula 3

$$(0.9\pm0.2)M_{2/n}O:Al_2O_3:wSiO_2:yH_2O$$

where "M" is at least one cation having a valence not more than 3, "n" represents the valence of "M", "w" is a value greater than about 3 up to 6, and "y" is a value up to about 9 depending upon the identity of "M" and the degree of hydration of the crystal. The $SiO_2/Al_2O_3$ mole ratio for Y zeolites can thus be from about 3 to about 6. Like the X zeolite, the cation "M" may be one or more of a variety of cations but, as the Y zeolite is initially prepared, the cation "M" is also usually predominately sodium. A Y zeolite containing predominately sodium cations at the exchangeable cationic sites is therefore referred to as a sodium-Y zeolite.

Cations occupying exchangeable cationic sites in the zeolite may be replaced with other cations by ion exchange methods well known to those having ordinary skill in the field of crystalline aluminosilicates. Such methods are generally performed by contacting the zeolite or a base material containing the zeolite with an aqueous solution of the soluble salt of the cation or cations desired to be placed upon the zeolite. After the desired degree of exchange takes place the sieves are removed from the aqueous solution, washed, and dried to a desired water content. By such methods the sodium cations and any non-sodium cations which might be occupying exchangeable sites as impurities in a sodium-X or sodium-Y zeolite can be partially or essentially completely replaced with other cations.

The term "base material" as used herein shall refer to a X or Y zeolite-containing material which can be used to make the special adsorbents described below. Generally the base material will be in the form of particles such as extrudates, aggregates, tablets, pills, macrospheres, or granules produced by grinding any of the above to a desired size range. The adsorbent to be used in our process will preferably have a particle size range of about 16-40 mesh (Standard U.S. Mesh). The X or Y zeolite can be present in the base material in concentrations generally ranging from about 75 wt. % to about 98 wt. % of the base material based on a volatile free composition. The remaining material in the base material generally comprises amorphous silica or alumina or both which is present in intimate mixture with the zeolite material. This amorphous material may be an adjunct of the manufacturing process of the X or Y zeolite (for example, intentionally incomplete purification of the zeolite during its manufacture) or it may be added to the relatively pure zeolite but in either case its purpose is to aid in forming or agglomerating particles of the zeolite. A suitable base material which can be used to make adsorbents for use in this process is "Molecular Sieves 13X" commercially available from the Linde Company, Tonawanda, N.Y.

We have surprisingly found that a certain X zeolite containing specified cations at the exchangeable cationic sites uniquely possesses the selectivity requirement and other necessary requirements previously discussed and is therefore suitable for use in the process. Specifically we have found that an adsorbent comprising a X zeolite containing potassium at the exchangeable cationic sites is suitable for use in our process. Such adsorbent may be manufactured by essentially completely ion exchanging "Molecular Sieves 13X" (Na-X zeolite) with potassium cations (typically with a KCl solution), washing the exchanged material with water to remove excess ion exchange solution and drying the adsorbent to less than about 10 wt. % measured by loss on ignition (LOI) at 900° C. The base material is deemed to be essentially completely exchanged when the residual sodium content of the adsorbent after ion exchange is less than about 2 wt. % $Na_2O$. We have unexpectedly discovered that many adsorbents predicted to be suitable for use in our process in fact either exhibit no selectivity for either an aldose or a ketose or show reverse selectivity, that is, selectivity for a ketose with respect to an aldose. Such adsorbents are not suitable for this process. An X zeolite containing potassium at the exchangeable cationic sites appears unique among the X zeolites in its ability to selectively adsorb an aldose with respect to a ketose. Considering, for instance, adsorbents comprising X zeolites containing at exchangeable cationic sites other cations of metals of Group IA of the Periodic Table of Elements, we have found that an adsorbent comprising a cesium-exchanged X zeolite exhibits selectivity for neither an aldose nor a ketose while an adsorbent comprising a sodium-X exhibits selectivity for a ketose with respect to an aldose. A potassium-exchanged Y zeolite, unlike the potassium-exchanged X zeolite, also exhibits selectivity for a ketose with respect to an aldose. Adsorbents comprising X zeolites containing at exchangeable cation sites either barium or strontium or barium and strontium or barium and potassium cations exhibit selectivity for a ketose with respect to an aldose while adsorbents comprising X zeolites containing at exchangeable cationic sites either calcium or magnesium exhibit selectivity for neither an aldose nor a ketose. The reasons why one adsorbent is acceptable for use in our process while others are not is not fully understood at the present time.

The adsorbent may be employed in the form of a dense compact fixed bed which is alternatively contacted with the feed mixture and desorbent materials. In the simplest embodiment of the invention the adsorbent is employed in the form of a single static bed in which case the process is only semi-continuous. In another embodiment a set of two or more static beds may be employed in fixed-bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589 incorporated herein by reference thereto. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of our process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well known to the separation art.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan on April 2, 1969, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° C. to about 200° C. with about 20° C. to about 100° C. being more preferred and a pressure range of from about atmospheric to about 500 psig. with from about atmospheric to about 250 psig. being more preferred to insure liquid phase. Desorption conditions will include the same range of temperatures and pressures as used for adsorption conditions.

The size of the units which can utilize the process of this invention can vary anywhere from those of pilot-plant scale (see for example our assignee's U.S. Pat. No. 3,706,812) to those of commercial scale and can range in flow rates from as little as a few cc. an hour up to many thousands of gallons per hour.

The following examples are presented to illustrate the unique selectivity relationship that makes the process of our invention possible and is not intended to unduly restrict the scope and spirit of the claims attached hereto.

EXAMPLE I

This example presents retention volume and selectivity results obtained by pulse tests with eleven adsorbents, one comprising an A zeolite, one comprising a Y zeolite, and nine comprising X zeolites. More specifically the adsorbent comprising the A zeolite was Linde 5A Molecular Sieves (a calcium-exchange A zeolite), the adsorbent comprising a Y zeolite was prepared by essentially completely ion-exchanging Linde SK-40 with potassium and the adsorbents comprising X zeolite were a portion of Linde 13X Molecular Sieves and portions of Linde 13X Molecular Sieves essentially completely exchanged with the cations of metals K, Cs, Mg, Ca, Sr, Ba, Ba+K and Ba+Sr. All adsorbents had a particle size range of approximately 20–40 U.S. Mesh.

The general pulse-test apparatus and procedure have been previously described. The adsorbents were tested in a 70 cc coiled column maintained at a process of 55° C. and 50 psig using pure water as the desorbent material. The sequence of operations for each test were as follows. Desorbent material (water) was continuously run through the column containing the adsorbent at a nominal liquid hourly space velocity (LHSV) of about 1.0. At a convenient time desorbent flow was stopped, a 4.7 cc sample of 10 wt. % fructose in water was injected into the column via a sample loop and the desorbent flow was resumed. The emergent sugar was detected by means of a continuous refractometer detector and a peak envelope trace was developed. Another pulse containing 10 wt. % glucose was similarly run. A saturated water solution of benzene was also injected to serve as a tracer from which the void volume of the adsorbent bed could be determined. Thus for each adsorbent tested three peak traces were developed, one for glucose, one for fructose and one for benzene. The retention volume for glucose is calculated by measuring the distance from time zero or the reference point to the midpoint of the glucose peak and subtracting the distance presenting the void volume of the adsorbent obtained by measuring the distance from the same reference point to the midpoint of the benzene peak. For some adsorbents both the fructose and glucose peaks were essentially on top of the benzene peak envelope indicating that both monosaccharides were relatively unadsorbed by the particular adsorbents in the presence of water. The selectivity (B), of an adsorbent for glucose with respect to fructose is the quotient obtained by dividing the glucose retention volume by the fructose retention volume. The results for these tests are shown in Table No. 1 below.

TABLE No. 1

Selectivities of Various Adsorbents for Glucose with Respect to Fructose

| TEST | ADSORBENT | RETENTION VOL. OF FRUCTOSE, CC. | RETENTION VOL. OF GLUCOSE, CC. | SELECTIVITY (B) |
|---|---|---|---|---|
| 1 | Na—X | 7.1 | 5.0 | 0.705 |
| 2 | K—X | 11.9 | 21.6 | 1.81 |
| 3 | K—Y | 10.8 | 4.9 | 0.453 |
| 4 | Cs—X | | Both were relatively unadsorbed | |
| 5 | Mg—X | | Both were relatively unadsorbed | |

TABLE No. 1-continued

Selectivities of Various Adsorbents for Glucose with Respect to Fructose

| TEST | ADSORBENT | RETENTION VOL. OF FRUCTOSE, CC. | RETENTION VOL. OF GLUCOSE, CC. | SELECTIVITY (B) |
|---|---|---|---|---|
| 6 | Ca—X | Both were relatively unadsorbed | | |
| 7 | Ca—A | Both were relatively unadsorbed | | |
| 8 | Sr—X | 8.0 | 1.3 | 0.163 |
| 9 | Ba—X | 27.1 | 9.6 | 0.354 |
| 10 | Ba—K—X | 16.4 | 7.5 | 0.456 |
| 11 | Ba—Sr—X | 21.3 | 4.2 | 0.200 |

The adsorbents used for tests 1 through 4 were three X zeolites and one Y zeolite each containing at the exchangeable cationic sites cations of metals from Group IA of the Periodic Table of Elements. The K-X adsorbent used for test 3 with a selectivity of 1.81 alone exhibited selectivity for glucose with respect to fructose. The K-Y and the Na-X adsorbents used for tests 1 and 3 respectively, with glucose to fructose selectivities of less than 1.0, showed reverse selectivity, that is, selectivity for fructose with respect to glucose while the Cs-X adsorbent used for test 4 exhibited selectivity for neither.

The adsorbents used for tests 5, 6, 8 and 9 were X zeolites containing at exchangeable cationic sites single cations of metals from Group IIA of the Periodic Table of Elements while the adsorbent used for test 7 was a calcium exchanged A zeolite (Linde 5A Molecular Sieves). As indicated by the results in Table 1 both glucose and fructose were relatively unadsorbed with the Mg-X, Ca-X, and Ca-A adsorbents used in the presence of water for tests 5, 6 and 7 respectively. Like the K-Y and Na-X adsorbents used for tests 1 and 3 respectively, both the Sr-X and Ba-X adsorbents used for tests 8 and 9 respectively also showed selectivity for fructose with respect to glucose rather than selectivity for glucose with respect to fructose. The adsorbents used for tests 10 and 11 were X zeolites containing at exchangeable cationic sites the cation pairs Ba and K and Ba and Sr respectively. These adsorbents also exhibited selectivity for fructose with respect to glucose.

EXAMPLE II

Additional pulse tests were run using a K-X adsorbent with the apparatus and procedure as described in Example 1 except that the column was maintained at a temperature of 60° C. and instead of employing pulses of solutions of pure components, i.e. separate pulses of pure glucose solution and pure fructose solution, pulses of a solution of a mixture of sugars were utilized having a composition comprising 5 percent each of fructose, glucose and sucrose. No tracer was used. The results are shown in the attached FIGURE. As clearly shown in the FIGURE sucrose was eluted first, then fructose and then glucose, demonstrating a clear separation of the three components, particularly glucose from fructose, as well as demonstrating that the highest relative selectivity of the K-X adsorbent is for the glucose component of the mixture.

The following calculations were made from the measurements of the plots in a manner described in the previous discussion:

|  | Glucose | Fructose |
|---|---|---|
| Band widths (cc) | 16.5 | 14.1 |
| Retention Vols. (cc) | 15.83 | 8.03 |

|  | Glucose | Fructose |
|---|---|---|
| B glucose/fructose = 1.97 | | |

Thus, the selectivity of the K-X adsorbent for the extract component (glucose) with respect to the raffinate component (fructose) is very close to the ideal value of 2.0.

EXAMPLE III

This example illustrates the ability of our process, when operated in a preferred embodiment, which utilizes a continuous simulated moving bed countercurrent type of operation, and comprises a pilot plant scale testing apparatus known as a carousel unit described in detail in deRosset et al U.S. Pat. No. 3,706,812, incorporated herein by reference. Briefly, the apparatus consists essentially of 24 serially connected adsorbent chambers having about 44 cc volume each. Total chamber volume of the apparatus is approximately 1,056 cc. The individual adsorbent chambers are serially connected to each other with relatively small diameter connecting piping and to a rotary type valve with other piping. The valve has inlet and outlet ports which direct the flow of feed and desorbent material to the chambers and extract and raffinate streams from the chambers. By manipulating the rotary valve and maintaining given pressure differentials and flow rates through the various lines passing into and out of the series of chambers, a simulated countercurrent flow is produced. The adsorbent remains stationary while fluid flows throughout the serially connected chambers in a manner which when viewed from any position within the adsorbent chambers is steady countercurrent flow. The moving of the rotary valve is done in a periodic shifting manner to allow a new operation to take place in the adsorbent beds located between the active inlet and outlet ports of the rotary valve. Attached to the rotary valve are input lines and output lines through which fluids to and from the process flow. The rotary valve contains a feed input line through which passes the isomerized feed mixture, and extract stream outlet line through which passes the desorbent material, i.e. water, in admixture with glucose, a desorbent material inlet line through which passes desorbent materials and a raffinate stream outlet line through which passes fructose and oligosaccharides in admixture with desorbent material. Additionally, a flush material inlet line is used to admit flush material for the purpose of flushing feed components from lines which had previously contained feed material and which will subsequently contain the raffinate or extract stream. The flush material employed is desorbent material which then leaves the apparatus as part of the extract stream and raffinate stream. Additional apparatus details can be found in U.S. Pat. No. 3,706,812. In order to better understand the operations taking place within the apparatus reference can be made to D. B. Broughton U.S. Pat. No. 2,985,589 and to D. B. Broughton et al, "The Separation of P-xylene from $C_8$ Hydrocarbon Mixtures by the Parex Process", presented at the Third Joint Annual Meeting, American Institute of Chemical Engineers and Puerto Rican Institute of Chemical Engineers, San Juan, Puerto Rico, May 17 through May 20, 1970. These references describe in detail the basic operations taking place in the testing apparatus used in this embodiment, and although said references are concerned with the separation of hydrocarbons, the testing apparatus itself is perfectly suited for purposes of this embodiment.

The feed mixture to the apparatus contained, in aqueous solution, 42 percent fructose, 53 percent glucose and 5 percent oligosaccharides. The adsorbent used was a potassium exchanged X faujasite.

The operating parameters of the carousel unit were as follows:

1. A/F=1.0, where A is the selective pore volume of the adsorbent in cc and F is the feed rate to the separation stage in cc/hr.
2. Process temperature=60° C.
3. Valve cycle time=1.0 hr.

Four tests, each of six hours duration, were conducted on the carousel unit. The rate of withdrawal of the extract stream was varied from test to test with all other parameters remaining constant. This variance affected the operation of the hereinbefore discussed purification zone. As the rate of withdrawal of the extract stream increased, the glucose concentration tended to decrease while the glucose yield, i.e. the percentage of the glucose in the feed mixture that was recovered in the extract stream, increased. Following are the results of the four tests:

| Test | Extract Stream Glucose Purity % Based on Dry Solids | Glucose Yield % |
| --- | --- | --- |
| 1 | 94 | 61 |
| 2 | 93 | 64 |
| 3 | 89 | 87 |
| 4 | 82 | 95 |

The oligosaccharides contained in the feed mixture were essentially all rejected into the raffinate with the fructose.

For comparison, the results of a carousel run using a Ca-Y adsorbent, with all other parameters the same as the first above run were as follows:

| Test | Extract Stream Fructose Purity % | Fructose Yield % |
| --- | --- | --- |
| 1 | 94 | 49 |
| 2 | 92 | 65 |
| 3 | 87 | 83 |
| 4 | 84 | 88 |

In this case the oligosaccharides were also rejected into the raffinate, but with the glucose.

Thus, it is clear from the above that it is the use of a K-X adsorbent which enables the separation of high purity glucose from a glucose-fructose mixture.

We claim as our invention:

1. A process for separating glucose from a mixture comprising glucose and fructose which process comprises the steps of:

(a) contacting said mixture at a temperature within the range of from 20° C. to 200° C. and a pressure from atmospheric pressure to 500 psig with an adsorbent comprising an X zeolite containing potassium cations at exchangeable cationic sites and selectively adsorbing said glucose in said adsorbent;

(b) removing from the adsorbent a raffinate stream comprising said fructose;

(c) contacting said adsorbent at a temperature within the range of from 20° C. to 200° C. and a pressure from atmospheric pressure to 500 psig with a desorbent material to effect the desorption of said glucose from said adsorbent; and, (d) removing from said adsorbent an extract stream comprising said glucose.

2. The process of claim 1 wherein it is effected in a liquid phase.

3. The process of claim 1 wherein said desorbent material is water.

4. A process for separating glucose from a mixture comprising glucose and fructose which process employs an adsorbent comprising an X zeolite containing potassium cations at exchangeable cationic sites which process comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said adsorption zone, said purification zone defined by the adsorbent located between an extract output stream at an upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed mixture into said adsorption zone at a temperature within the range of from 20° C. to 200° C. and a pressure within the range of from atmospheric to 500 psig and effecting the selective adsorption of said glucose by said adsorbent in said adsorption zone and withdrawing a raffinate output stream from said adsorption zone;

(f) passing a desorbent material into said desorption zone at a temperature within the range of from 20° C. to 200° C. and a pressure within the range of from atmospheric to 500 psig to effect the displacement of said glucose from the adsorbent in said desorption zone;

(g) withdrawing an extract output stream comprising said glucose and desorbent material from said desorption zone;

(h) passing a portion of said extract output stream to a separation means and therein separating at separation conditions a portion of said desorbent material to produce a glucose product stream having a reduced concentration of desorbent material; and, (i) periodically advancing through said column of adsorbent in a downstream direction with respect to fluid flow in said adsorption zone the feed input stream raffinate output stream, desorbent input stream, and extract output stream to effecting the shifting of zones through said adsorbent and the production of extract output and raffinate output streams.

5. The process of claim 4 wherein the process is effected in a liquid phase.

6. The process of claim 4 wherein the process includes the step of passing at least a portion of said raffinate output stream to a separation means and therein separating at separation conditions at least a portion of said desorbent material to produce a raffinate product having a reduced concentration of desorbent material.

7. The process of claim 4 wherein the process includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

8. The process of claim 4 wherein said desorbent material is water.

* * * * *